United States Patent
Ninane et al.

(10) Patent No.: US 9,089,273 B2
(45) Date of Patent: Jul. 28, 2015

(54) TEXTILE ELECTRODE

(75) Inventors: Christian Ninane, Liege (BE);
Benjamin Deliege, Verviers (BE)

(73) Assignee: CECOTEPE ASBL, Seraing (BG)

( * ) Notice: Subject to any disclaimer, the term of this patent is extended or adjusted under 35 U.S.C. 154(b) by 127 days.

(21) Appl. No.: 13/809,510

(22) PCT Filed: Jul. 8, 2011

(86) PCT No.: PCT/EP2011/061618
§ 371 (c)(1),
(2), (4) Date: Mar. 18, 2013

(87) PCT Pub. No.: WO2012/007384
PCT Pub. Date: Jan. 19, 2012

(65) Prior Publication Data
US 2013/0172722 A1     Jul. 4, 2013

(30) Foreign Application Priority Data

Jul. 13, 2010   (EP) .................................... 10169351

(51) Int. Cl.
*A61B 5/0478*   (2006.01)
*A61B 5/0408*   (2006.01)
*A61B 5/00*     (2006.01)

(52) U.S. Cl.
CPC .......... *A61B 5/0478* (2013.01); *A61B 5/04085* (2013.01); *A61B 5/4806* (2013.01); *A61B 5/6803* (2013.01); *A61B 5/6804* (2013.01)

(58) Field of Classification Search
CPC .................................................... A61B 5/0478
USPC .......... 600/382–384, 386, 388, 397, 390.397
See application file for complete search history.

(56) References Cited

U.S. PATENT DOCUMENTS

| | | | |
|---|---|---|---|
| 3,845,757 A | 11/1974 | Weyer | |
| 3,954,100 A * | 5/1976 | Sem-Jacobsen | 600/393 |
| 6,970,731 B1 * | 11/2005 | Jayaraman et al. | 600/388 |
| 7,373,196 B2 * | 5/2008 | Ryu et al. | 600/372 |
| 7,532,921 B2 * | 5/2009 | Eichler | 600/372 |
| 7,747,303 B2 * | 6/2010 | Eichler | 600/390 |
| 7,966,052 B2 * | 6/2011 | DeFusco et al. | 600/386 |
| 2004/0138546 A1 * | 7/2004 | Reho et al. | 600/382 |
| 2007/0078324 A1 | 4/2007 | Wijisiriwardana | |
| 2008/0154111 A1 | 6/2008 | Wu et al. | |
| 2009/0076362 A1 * | 3/2009 | Jaatinen | 600/372 |
| 2009/0105577 A1 | 4/2009 | Wu et al. | |
| 2009/0203984 A1 * | 8/2009 | Dias et al. | 600/388 |

FOREIGN PATENT DOCUMENTS

| | | |
|---|---|---|
| WO | WO 01/02052 A2 | 1/2001 |
| WO | WO 2004/058346 A1 | 7/2004 |
| WO | WO 2007/092290 A2 | 8/2007 |
| WO | WO 2008/022482 A1 | 2/2008 |
| WO | WO 2008/109699 A2 | 9/2008 |
| WO | WO 2009/013704 A2 | 1/2009 |

\* cited by examiner

*Primary Examiner* — Lee S Cohen
(74) *Attorney, Agent, or Firm* — Reinhart Boerner Van Deuren P.C.

(57) ABSTRACT

The present invention is related to a textile electrode (1) for measuring an electrical signal from a body part, said electrode comprising, successively from the side to be applied on the body part to the outside: a conductive textile contact (3) to be applied to said body part; a textile support (2) for supporting said textile contact (3); a vapor barrier sheet material (7) able to reduce, in use, evaporation of liquid from said textile electrode (1).

12 Claims, 3 Drawing Sheets

TEXTILE ELECTRODE

FIELD OF THE INVENTION

The present invention is related to a textile electrode for measuring an electrical signal from a body part.

Another aspect of the invention is related to a clothing comprising such an electrode.

STATE OF THE ART

Medical electrodes are known in the art. Usually, those electrodes comprise a metallic surface in close contact with the skin. They are fixed on the skin by means of an adhesive, and the impedance between the skin and the metallic surface is reduced by the use of a conductive gel, for example silver gel or the use of a sponge-like material filled with an aqueous solution containing an electrolyte. Such type of electrodes is for example disclosed in document U.S. Pat. No. 3,845,757. Such type of electrodes will be referred hereafter as standard medical electrodes, or prior art medical electrodes.

Prior art medical electrodes suffer several drawbacks. For example, particular care is to be taken to obtain good adhesion between the skin and the electrode (i.e. the skin should be shaved and cleaned). In order to avoid failure of the adhesive, for example, the conductive gel should not contaminate the adhesive surface, as it can inhibit the adhesion. Finally, the use of such electrode is somewhat uncomfortable. This is particularly true for long term measurement, for example in the field of sleepiness studies.

WO-A-01/02052 discloses a garment, adapted to be used as a medical electrode. The garment comprises a tubular body, which comprises at least two different zones. One of these zones is an electrically conductive zone, to be used as the electrode surface of the medical electrode. Another zone is an elastic zone, which comprises electrically non-conductive yarns. This elastic zone assures the position of the electrically conductive zone on the corpus on which the medical electrode is to be used.

It is known that the contact electrical resistance between such textile based electrode and the skin of a wearer to which the electrode is applied is high enough to render detection of electrical signals difficult. The contact electrical resistance in that case is further negatively impacted by the wearer movements, reducing the signal-to-noise ratio. This can be partly reduced by the presence of moisture, due either to perspiration in case of measurements during sport exercise, or to the addition of a conductive gel applied on the electrode.

Unfortunately, perspiration is not always present, and the addition of gel has only a transient effect, as the gel solvent has a tendency to evaporate. The disclosed electrode is therefore not suitable for measuring small electrical signals such as EEG, in a long term experiment and more particularly with patient at rest. On the one hand, such EEG measurements are key data in the study for example of sleepiness, wherein, on the other hand, the modification of the comfort of the sleeper should be as small as possible.

Document WO 2004/058346 discloses an electrode arrangement wherein the conductive contact with the skin is obtained with a moisture impermeable electrode, thereby maximising the appearance of perspiration and reducing contact resistance. Again, due to its rigidity, this electrode is a bit uncomfortable and not suitable for a user at rest or relaxed, or in skin parts producing a small amount of perspiration such as the human head in normal rest conditions where the patient is not stressed.

AIMS OF THE INVENTION

The present invention aims to provide a textile electrode that overcomes the drawbacks of prior art.

More particularly, the present invention aims to provide a textile electrode able to measure small electrical signals such as EEG signals in long term experiment, preferably lasting more than 12 hours.

Furthermore, the present invention aims to provide a textile electrode complying with usual sleeping conditions.

SUMMARY OF THE INVENTION

The present invention is related to a textile electrode for measuring an electrical signal from a body part, said electrode comprising, successively from the side to be applied on the body part to the outside:
  a conductive textile contact to be applied to said body part;
  a textile support for supporting said textile contact;
  a vapour barrier sheet material able to reduce, in use, evaporation of liquid from said textile electrode.

According to particular preferred embodiments, the invention further discloses at least one or a suitable combination of the following features:
  the water vapour transmission rate of the vapour barrier sheet material is lower than 100 g/m²·day;
  the water vapour transmission rate of the vapour barrier sheet material is lower than 50 g/m²·day;
  the textile contact is impregnated with a conductive gel;
  the textile electrode further comprises an absorbent material able to store a liquid or a gel, said absorbent material being disposed between said conductive textile and said textile support;
  the absorbent material is impregnated with the conductive gel, or with a solvent of the conductive gel;
  an outer electrical contact is connected to the conductive textile contact and located on the external side of said barrier sheet material;
  the vapour barrier sheet material comprises a polymeric layer;
  the polymeric layer comprises a polymer selected from the group consisting of PEEK, polyimide, polyamide-imide, polyethersulfone, polysulfone, liquid crystalline polymers, polyester and their blends;
  the polymeric layer comprises a polymer selected from the group consisting of EPDM, ethylene vinyl acetate, SIS, SEBS, ethylene-propylene-rubber, synthetic or natural rubber, their copolymers and their blends;
  the vapour barrier sheet material further comprises a metallic or a metal oxide layer;
  an electrical circuit is printed onto said metallic layer;
  the textile electrode further comprises electronic devices for treating, in use, the signal induced by said body part;
  said electronic devices comprise amplification means and/or wireless communication means;
  the vapour barrier sheet material is flexible;
  the barrier sheet material is attached on the textile support by means of an adhesive and/or by sewing it along its perimeter on the textile support.

Another aspect of the invention is related to a clothing comprising at least one electrode according to the invention.

Preferably, the clothing of the invention is suitable for disposing said electrode in contact with the head of a patient.

The present invention is also related to the use of a clothing according the invention for measuring an EEG signal or an EMG signal.

FIGURE KEYS

Figure 1:
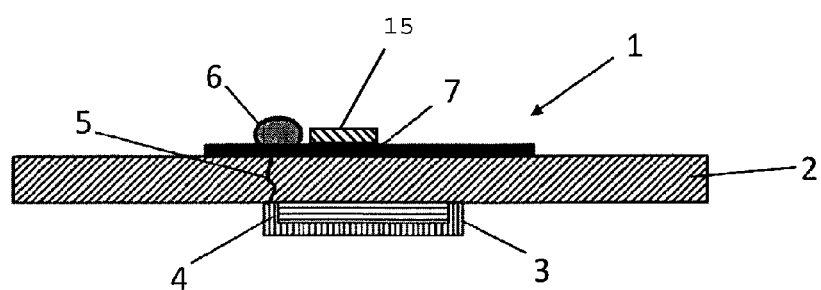
FIG. 1 schematically represents a cross-section view of an example of a textile electrode according to the present invention.

1. Electrode
2. Textile support
3. Conductive textile contact
4. Liquid absorbing material
5. Electrical wire
6. Outer electrical contact
7. Barrier sheet material
8. Clothing
9. Connection wires
10. EEG interface
11. Patient's head
12. AC Voltage source
13. Oscilloscope
14. Resistance

DETAILED DESCRIPTION OF THE INVENTION

The electrode of the present invention comprises a conductive textile 3, for example made of conductive silver thread, for providing a contact with the skin. When placed on the skin, and due to its softness, such a contact improves the comfort of the wearer in comparison to rigid contacts.

In order to dispose the contact in the right place on a body part where an electrical signal has to be measured, the conductive contact is supported by a textile 2. In order to improve the comfort of the device, and improve the stability of the obtained contact, support textile has preferably elastic properties. This can be obtained for example by the use of a knitted jersey, using conventional fibres.

In order to increase the electrical contact between the skin and the conductive textile, the conductive textile is preferably impregnated by a conductive gel or a conductive liquid. As such liquid or gel are generally volatile, the impregnation is usually performed just before use. The use of such liquids or gels reduces the contact impedance of the electrode in such a way that very small electrical signals, such as those measured in EEG, can be easily measured.

In order to reduce the evaporation of the gel solvent, which degrades the quality of the electrical contact, a moisture barrier sheet material 7 is applied on the back side of the textile support 2. It was then discovered that the latter considerably reduces the evaporation of the conductive gel or gel solvent, thereby improving the possible time of continuous measurement. Such moisture barrier sheet material would advantageously extend on a surface a bit larger than the underlying conductive textile contact 3, in order to minimise the solvent evaporation. A barrier sheet having dimensions 10% to 20% larger than the contact is a good compromise between evaporation reduction and comfort improvement.

Preferably, the barrier sheet material has a water vapour transmission rate (WVTR), also called moisture vapour transmission rate (MVTR), lower than about 100 g/m$^2$·day, more preferably lower than about 50 g/m$^2$·day, ideally lower than about 25 g/m$^2$·day. WVTR in the present invention is measured according to ASTM E-96-92.

Advantageously, the support textile 2 is hydrophobic, in order to reduce lateral migration of the liquid by capillarity.

To further improve the possible continuous measurement time, an additional quantity of conductive gel or gel solvent can advantageously be stored in an intermediate absorbing layer 4. This layer can be either a sponge-like material or, preferably, an additional textile layer. This additional textile layer can preferably be obtained by 3 dimensional weaving. Advantageously, this absorbing layer is hydrophilic, in order to store a high quantity of solvent, thereby increasing the possible measurement time. Such an electrode is represented in FIG. 1.

This additional layer can also improve the electrical contact by having the sensing surface on a protrusion standing out of the textile surface.

Advantageously, the barrier sheet material will exhibit elastomeric properties, in order to reduce the impact on the mechanical properties of the device. This can be obtained by the use of polymers selected from the group consisting of EPDM, ethylene vinyl acetate, SIS, SEBS, ethylene-propylene-rubber, synthetic or natural rubber, their copolymers and their blends. Alternatively, the barrier sheet material can comprise a polymer selected from the group consisting of PEEK, polyimide, polyamide-imide, polyethersulfone, polysulfone, liquid crystalline polymers such as those commercialised under the tradename Vectra®, polyester and their blends. These last polymers are suitable as the supporting layer for making flexible printed circuit board.

In order to increase its barrier properties, the barrier sheet material is advantageously a multilayer film comprising a vapour barrier material. Preferably, at least one layer of said multilayer film is a metallic or metal oxide layer.

More preferably, the outer layer (the layer on the side opposed to the textile on which the barrier sheet is fixed) is a metallic layer. This metallic layer, additionally to the barrier improvement, may advantageously be used to produce a printed circuit board on the back side of the electrode. In that case, the metallic area left after printing will reduce the effective area available for water vapour transmission, reducing the total evaporation rate of the electrode.

In order to simplify the connection of the electrode 1 to an acquisition device 10, an outer electrical contact 6 can be available on the back side of the moisture barrier sheet material 7. This contact can be connected to the conductive textile contact 3 by means of an electrical wire 5. The connection between the contact 6 and the acquisition device 10 can then be assured by means of a wire 9, or any other communication means.

Preferably, the barrier sheet material comprises on its back side a printed circuit board (PCB) 15, more preferably, a flexible PCB 15. This permits to provide an electronic circuit directly placed on the electrode. For example, the circuit may comprise amplification means such as a differential amplifier closest to the contact. This proximity may reduce the noise level, thereby improving the signal-to-noise ratio. In a particular embodiment, the electrode may be reduced to this mere circuit but with the disadvantage that the textile sensation is much more comfortable for the skin and that the textile structure is more favourable for the gel repartition.

Figure 2:
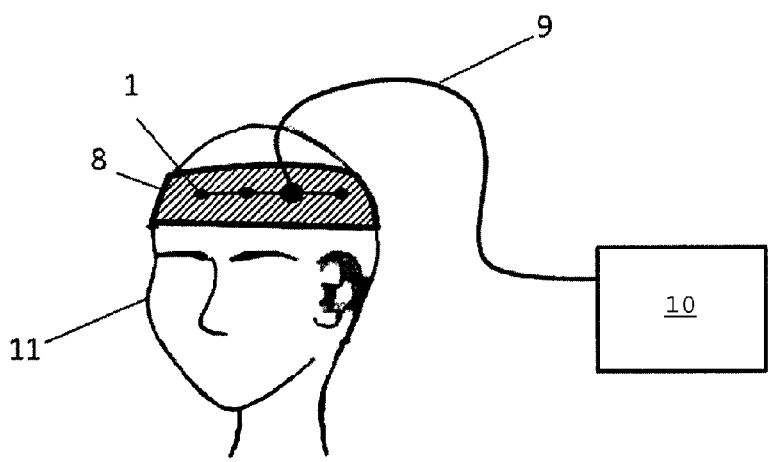
FIG. 2 schematically represents an example of a clothing (head band) including textile electrodes according to the invention.

The electrode of the present invention can advantageously be integrated in a wearable clothing 8, as schematically represented in FIG. 2. Preferably, said clothing 8 exhibits high elasticity, in order to regulate the pressure applied between the conductive textile 3 and the body part. This clothing 8 can advantageously comprise further elements, such as accumulators, signal recorder and/or wireless communication devices, so that no wire has to be connected to external devices upon use, thereby further improving the comfort of the wearer.

All those advantages render the clothing of the present invention particularly adapted to EEG measurements in sleepiness studies, particularly by reducing the sleeper perturbation arising from the different connections to external devices needed in such experiment. In such studies, minimum measurement time and user comfort are key parameters. For that reason, the electrodes of the present invention may advantageously be integrated in a bonnet or a hat-like clothing.

The clothing of the present invention may also be advantageously for use in pediatric studies.

It is also to be noticed that the gel impregnation is easier in the electrode of the invention and may be performed by an untrained user without risk, contrary to prior art medical electrodes wherein bad positioning of the gel may reduce the adhesion of the electrode. In the electrode of the invention, this adhesion and the resulting quality contact is better secured by the elastic pressure applied by the elasticity of the textile used.

EXAMPLE

Figure 3:
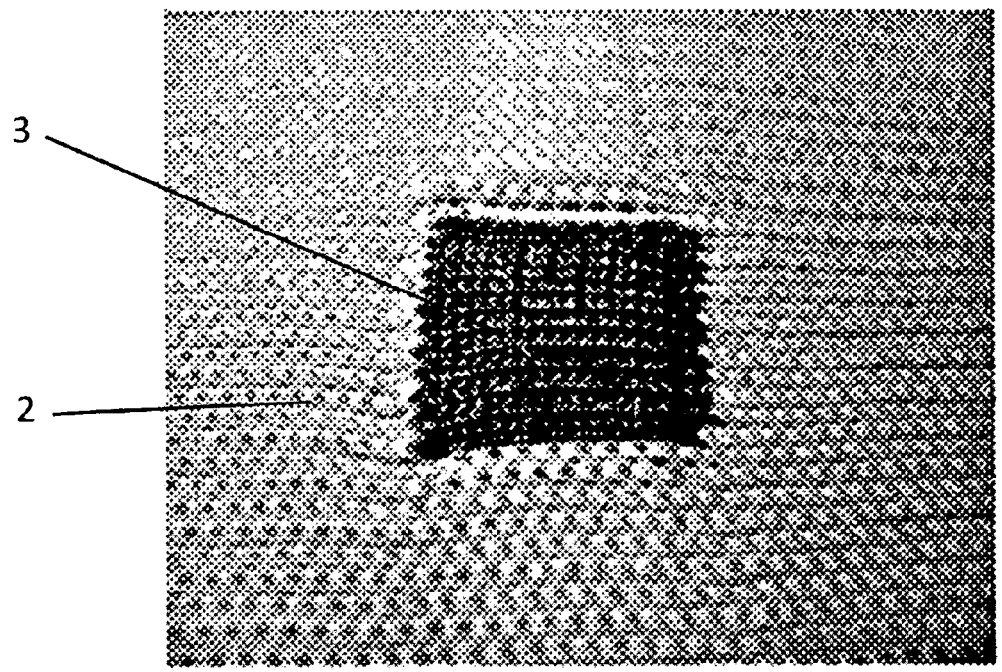
FIG. 3 represents a picture of an electrode according to the invention.

Three examples of electrodes according to the invention have been produced, and their performance has been compared with standard medical electrodes. FIG. 3 represents a picture of one of those electrodes.

As seen in FIG. 3, the textile contacts are integrated in jersey textile. The textile structure is, from skin contact to outer side: conductive textile/support textile/barrier sheet material.

The conductive textile is a double knitted jersey incorporating polyamide fibres coated with silver (Shieldex 235/34dtex 2 ply HC). The supporting textile is an interlock polyester jersey, acting also as an isolating layer. And, finally, the barrier sheet layer is a dielectric polyimide (Kapton™) film of 50 μm, with a superimposed copper layer of 35 μm (PCB flex). The PCB sheet is extending 0.5 cm away from the limits of the subjacent contact area.

According to WVTR reported in the literature, 50 μm Kapton films have a WVTR of lower than about 27 g/m$^2$·day (largest reported value). This value is further reduced by the presence of the metalized area left by the PCB, a 35 μm copper layer being considered as an absolute barrier layer.

The conductive gel is a silver containing gel, commercialised under the tradename "Brygel ECG". The latter is a commonly used gel in the field of EEG measurement.

Figure 4:
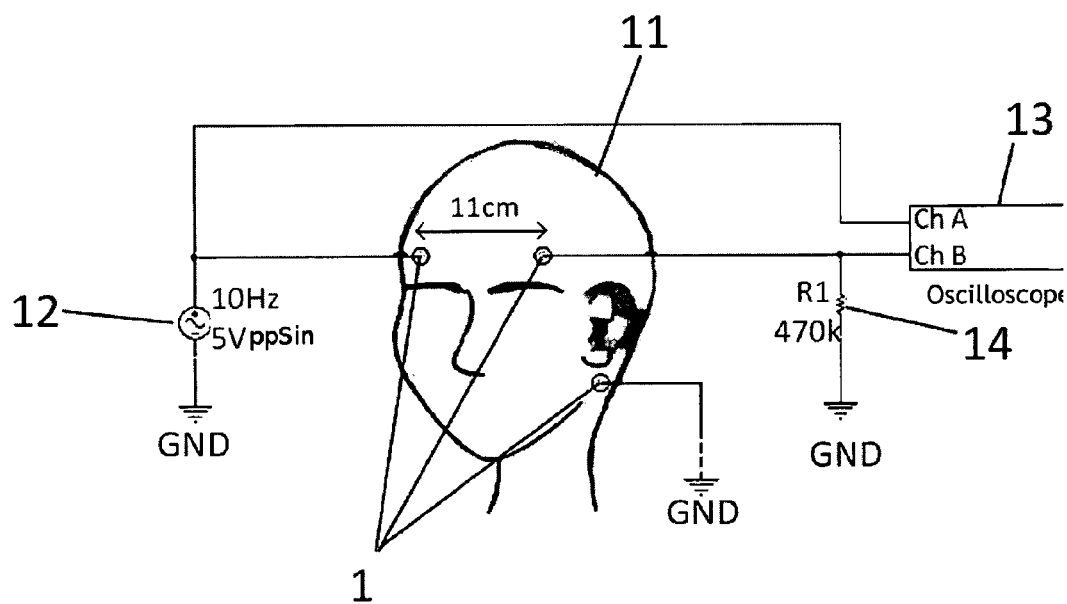
FIG. 4 schematically represents the experimental testing setup of an example of textile electrode according to the invention.

Two electrodes are integrated in the support, which has the shape of an elastic band, having a tuneable length. The general electric setup is represented in FIG. 4. The distance between the electrodes is approximately 11 cm and the electrodes are maintained on the forehead of a patient with a constant pressure. An additional ground electrode is placed on the wearer skin. A sinusoidal signal of 5 Vpp is injected from the AC voltage source 12 in the first electrode. At the output of the second electrode a resistance 14 is placed having a magnitude order similar to that of the impedance to be measured. Measurements are performed with an oscilloscope 13.

When conductive gel is used in the impedance measurement, about 0.5 g is deposited directly on the contact before the measurement.

In all impedance measurements, a quasi static impedance has been measured by means of a 10 Hz signal. In order to evaluate the noise level, the 50 Hz signal arising from the electric distribution system has been measured.

Three textile electrodes dimensions have been used, having respectively 1, 2 and 4 square cm. The impedance has been measured on both dry electrodes, and on electrodes with gel. The results obtained by those electrodes have been compared with a prior art medical electrode having a gel contact area of about 2 square cm and a metallic electrode of 0.8 square cm. No measurements were performed on dry prior art medical electrodes. The results are summarised in table 1.

TABLE 1

|  | Prior art medical electrode | Textile 1 cm2 | Textile 2 cm2 | Textile 4 cm2 |
| --- | --- | --- | --- | --- |
| Dry electrode 10 Hz | — | 505 kΩ | — | 40.4 kΩ |
| With Gel 10 Hz | 10 kΩ | 47 kΩ | — | 7.4 kΩ |
| With gel, 100 Hz | 8.9 kΩ | 21.45 kΩ | 13.5 kΩ | 6.2 kΩ |
| 1 kHz with gel | 4.2 kΩ | 5.6 kΩ | 3.7 kΩ | 1.6 kΩ |
| 10 kHz with gel | 0.832 kΩ | 0.654 kΩ | 0.54 kΩ | 0.33 kΩ |

The results in table 1 show that all the proposed surfaces are acceptable, with a surface of 3.25 square cm for obtaining the properties closest to the prior art medical electrodes (usual standard).

The noise arising from 50 Hz electric distribution has also been estimated. Table 2 summarise the (unwanted) 50 Hz measured voltage amplitude of the raw signal component (units: volt).

TABLE 2

|  | Prior art medical electrode | Textile 1 cm2 | Textile 4 cm2 |
| --- | --- | --- | --- |
| Dry electrode | — | 0.156 | 0.064 |
| With Gel | 0.03 | 0.052 | 0.016 |

Figure 5:
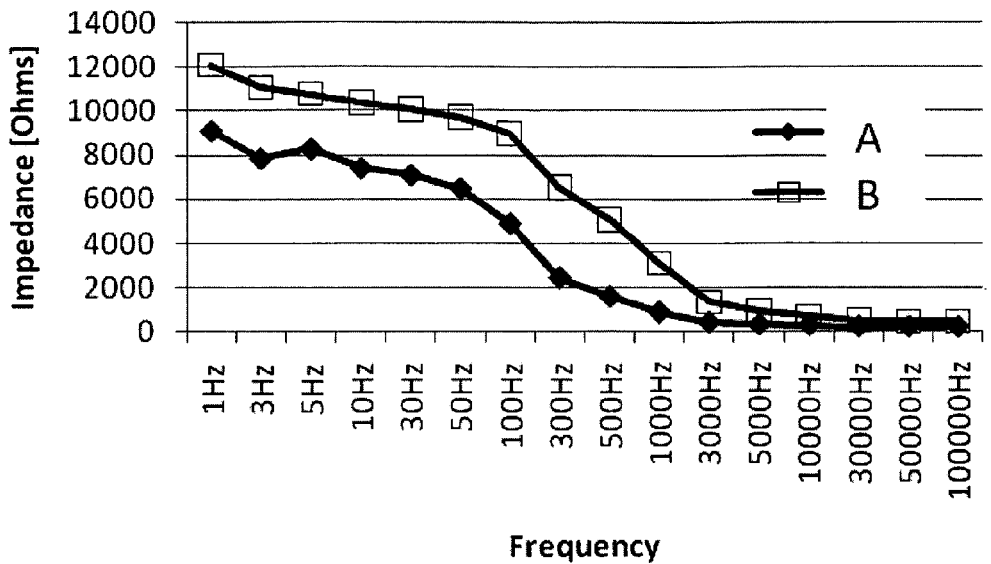
FIG. 5 represents a comparison of the impedance of an electrode according to the invention and a prior art medical electrode respectively, as a function of frequency.

FIG. 5 represents the impedance variation of the textile electrode of a 4 square cm conductive textile contact according to the invention (curve A) compared to the impedance of the prior art medical electrode (curve B), over a large range of frequencies. These results demonstrate the ability of such electrode to record electrical signal over a wide frequency range. By means of the embedded electronics as described above, the direct impedance of the electrode according the invention can even be reduced as compared with the prior art medical electrode, with a noise level also reduced.

Figure 6:
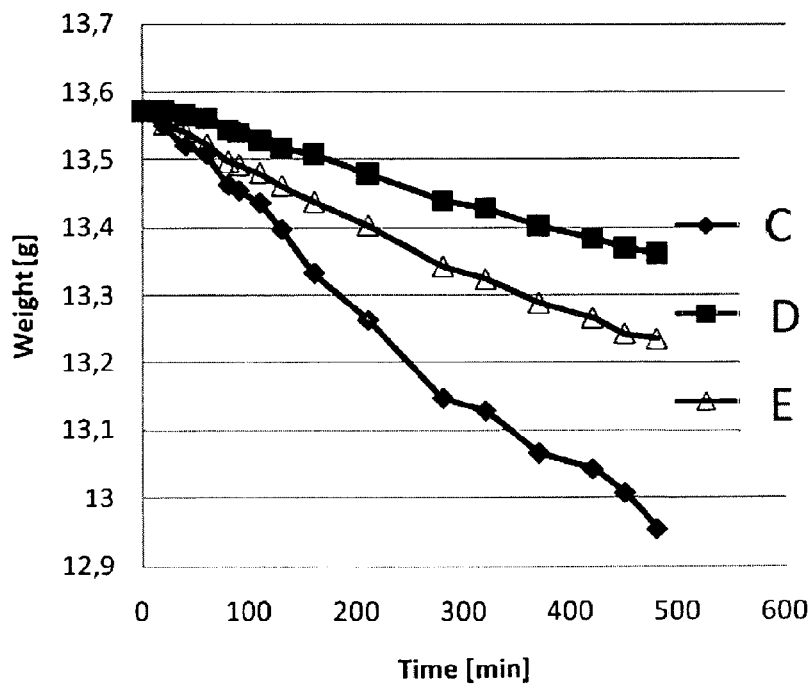
FIG. 6 represents weight loss measurement of different electrode arrangements (gel solvent losses).

FIG. 6 represents the weight loss of different electrode setups as a function of time. In all cases, about 1 g of conductive gel has been deposited on the electrode, and each electrode has been disposed on a moisture impermeable surface. Curve C represents the weight loss in the case of a textile electrode without a moisture barrier sheet material on the back side. Curve D represents the case when the back side barrier sheet material is adhesively positioned by means of glue on almost the entire surface of the barrier sheet material. Curve E represents the weight loss in the case of a conductive textile electrode with a moisture barrier sheet material sewed on the back side of the electrode. In E, the sewed area is located in the perimeter of the barrier film. In order to mechanically secure the electrode of the invention, the use of both adhesive bonding and sewing the perimeter is preferred. One sees that the variation of the weight of gel with time is much stronger in the case of an electrode without a moisture barrier sheet (curve C). The difference between curves D and E is that, in the bonded case, the meshes are maintained much more tight, which further reduces the loss of gel moisture. Qualitatively, for the two electrodes with moisture barrier, the remaining gel is of similar aspect as the gel initially deposited. In the case without moisture barrier, the gel becomes dry and sticky.

The invention claimed is:

1. Textile electrode for measuring an electrical signal from a body part, said electrode comprising, successively from an inner side to be applied on the body part to an outer side:
   a conductive textile contact to be applied to said body part;
   a textile support for supporting said textile contact;
   a vapour barrier sheet material able to reduce, in use, evaporation of liquid from said textile electrode, wherein the water vapour transmission rate of the vapour barrier sheet material is lower than 50 g/m$^2$·day; and
   wherein the textile support extends beyond the vapour barrier sheet material.

2. Textile electrode according to claim 1, wherein said textile contact is impregnated with a conductive gel.

3. Textile electrode according to claim 1, further comprising an absorbent material able to store a liquid or a gel, said absorbent material being disposed between said conductive textile contact and said textile support.

4. Textile electrode according to claim 3, wherein said absorbent material is impregnated with a conductive gel, or with a solvent of the conductive gel.

5. Textile electrode according to claim 1, wherein an outer electrical contact is connected to the conductive textile contact and located on an external side of said barrier sheet material.

6. Textile electrode according to claim 1, wherein the vapour barrier sheet material comprises a polymeric layer.

7. Textile electrode according to claim 6, wherein the polymeric layer comprises a polymer selected from the group consisting of polyimide, polyamide-imide, polyethersulfone, polysulfone, liquid crystalline polymers, polyester and their blends.

8. Textile electrode according to claim 6, wherein the polymeric layer comprises a polymer selected from the group consisting of EPDM, ethylene vinyl acetate, SIS, SEBS, ethylene-propylene-rubber, synthetic or natural rubber, their copolymers and their blends.

9. Textile electrode according to claim 6, wherein the vapour barrier sheet material further comprises a metallic or a metal oxide layer.

10. Textile electrode according to claim 9, wherein an electrical circuit is printed onto said metallic layer.

11. Textile electrode according to claim 10, wherein said electrical circuit comprises an amplifier and/or a wireless communication device.

12. A wearable clothing comprising a head band configured to be worn on the head of a patient, wherein said head hand comprises at least one electrode according to claim 1, and wherein said head band is suitable for disposing said electrode in contact with the head of the patient.

* * * * *

UNITED STATES PATENT AND TRADEMARK OFFICE
CERTIFICATE OF CORRECTION

| | | |
|---|---|---|
| PATENT NO. | : 9,089,273 B2 | Page 1 of 1 |
| APPLICATION NO. | : 13/809510 | |
| DATED | : July 28, 2015 | |
| INVENTOR(S) | : Christian Ninane et al. | |

It is certified that error appears in the above-identified patent and that said Letters Patent is hereby corrected as shown below:

In the claims:

Col. 8, lines 29-30, claim 12, the term "said head hand" should be --said head band--

Signed and Sealed this
Eighth Day of December, 2015

Michelle K. Lee
*Director of the United States Patent and Trademark Office*